United States Patent
Yamamoto

(10) Patent No.: US 8,733,273 B2
(45) Date of Patent: May 27, 2014

(54) ADHESIVE EJECTING APPARATUS

(75) Inventor: Hiroki Yamamoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 485 days.

(21) Appl. No.: 12/715,995

(22) Filed: Mar. 2, 2010

(65) Prior Publication Data

US 2010/0212814 A1  Aug. 26, 2010

(30) Foreign Application Priority Data

Mar. 2, 2009 (JP) ............................. P 2009-048653
Feb. 26, 2010 (JP) ............................. P2010-041933

(51) Int. Cl.
*B05B 1/30* (2006.01)
*B05B 7/06* (2006.01)
*B05C 5/00* (2006.01)

(52) U.S. Cl.
USPC ........... 118/314; 118/300; 118/313; 118/315; 118/324; 118/325

(58) Field of Classification Search
USPC .......................... 118/300, 313–315, 324–325
See application file for complete search history.

(56) References Cited

U.S. PATENT DOCUMENTS 4,949,668 A * 8/1990 Heindel et al. ................ 118/314

FOREIGN PATENT DOCUMENTS

| CN | 1424448 A | 6/2003 |
|---|---|---|
| JP | 1164463 A | 6/1989 |
| JP | 3296463 A | 12/1991 |
| JP | 7185413 A | 7/1995 |
| JP | 2619595 B2 | 3/1997 |
| JP | 2005329283 A1 | 2/2005 |

OTHER PUBLICATIONS

Office Action issued in corresponding Mexican Patent Application No. MX/A/2010/002490, which issued on Dec. 5, 2012—English Language Version.
Office Action issued in corresponding Mexican Patent Application No. MX/A/2010/002490, which issued on Dec. 5, 2012—Mexican Language Version.
Office Action issued on Mar. 7, 2013 for counterpart Colombian Patent Application File No. 11 121351.
Office Action dated Apr. 12, 2013.
Office Action mailed Sep. 12, 2013, corresponds to Chinese patent application No. 201080010109.3.
Office Action as issed on Jun. 22, 2013 in the counterpart EG Patent Application No. 1463/2011.
Office Action issued Jun. 11, 2013 corresponds to Mexican patent application No. MX/a/2010/002490.

* cited by examiner

*Primary Examiner* — Dah-Wei D Yuan
*Assistant Examiner* — Stephen Kitt
(74) *Attorney, Agent, or Firm* — Lowe Hauptman & Ham LLP

(57) ABSTRACT

An ejecting mechanism includes a pump, a pump controller unit, a distribution pipe, a restricting unit, and adhesive nozzles. The pump controller unit is configured to control to increase or decrease the amount of adhesive to be taken in by the pump. The distribution unit is configured to send a predetermined amount of adhesive to the adhesive nozzles out of the adhesive supplied by the pump, and to return the rest of adhesive to a discharge pipe out of the supplied adhesive, except for the predetermined amount of adhesive. The restricting unit is configured to disposed between the distribution unit and the discharge pipe and configured to restrict an amount of adhesive to be returned to a pipe.

12 Claims, 4 Drawing Sheets

ADHESIVE EJECTING APPARATUS

TECHNICAL FIELD

The present disclosure relates to an adhesive ejecting apparatus for ejecting adhesive toward a to-be-joined member.

BACKGROUND ART

An absorbent article, such as a pants-type disposable diaper, generally includes a front waistline region to be fitted to the front waistline of a wearer, a back waistline region to be fitted to the back waistline of the wearer, a crotch region to be fitted to the crotch of the wearer, and leg-surrounding regions (for example, leg holes) respectively at sides of the crotch region.

Such an absorbent article is formed mainly of: a liquid-permeable top sheet configured to come into contact with the skin of a wearer; a back sheet provided outside of the top sheet; and an absorber provided between the top sheet and the back sheet and configured to absorb excretion of the wearer.

The top sheet, the back sheet, and the absorber are bonded together with adhesive.

In consideration of the wear comfort of the absorbent article to the wearer, it is desirable that the adhesive be applied in a small amount.

For example, a technique to apply adhesive in a small amount onto an absorbent article has been disclosed (refer to PTL 1). In the known technique, adhesive is applied onto a web continuously in a predetermined pattern by partially and periodically opening and closing a plurality of small holes provided in a nozzle.

The inventors have discovered that, in the known technique, the internal pressure in the nozzle increases while the small holes are closed. As a result, immediately after the small holes are opened, a large amount of adhesive is likely to be ejected.

When a plurality of small holes provided in the nozzle are partially and periodically opened and closed, the ejection amount and ejection pressure may be destabilized to cause adhesive application failure.

There is a need to provide an adhesive ejecting apparatus capable of applying adhesive in a small amount yet uniformly.

CITATION LIST

Patent Literature

PTL 1. Japanese Patent No. 2619595 (p. 4; FIG. 2 and FIG. 5)

SUMMARY

Therefore, the present invention has been made in consideration of the above problems. It is an object of the present invention to provide an adhesive ejecting apparatus capable of applying adhesive in a small weight uniformly onto a to-be-joined member.

In an aspect of the present invention, an adhesive ejecting apparatus includes: a reservoir unit, a flow pipe, at least an ejecting mechanism. The reservoir unit is configured to store adhesive to be applied onto a to-be-joined member. The reservoir unit comprises: an outlet through which the adhesive stored in the reservoir unit is sent out to the ejecting mechanism, and an inlet through which the adhesive flowing through the flow pipe is returned to the reservoir unit. The flow pipe has one end connected to the outlet and another end connected to the inlet, so that the adhesive stored in the reservoir unit flows through the flow pipe. The ejecting mechanism is connected to the flow pipe and configured to eject the adhesive toward the to-be-joined member. The ejecting mechanism includes: at least an ejector unit configured to eject the adhesive toward the to-be-joined member; a supply unit configured to supply the ejector unit with the adhesive flowing through the flow pipe; a distribution unit configured to send a predetermined amount of adhesive supplied by the supply unit to the ejector unit, and to return the rest of the supplied adhesive to the flow pipe; and a restricting unit disposed between the distribution unit and the flow pipe and configured to restrict an amount of adhesive to be returned to the flow pipe. The supply unit is configured to supply adhesive from the flow pipe to the ejector unit in an amount larger than a specified ejection amount of adhesive to be ejected by the ejector unit.

According to the characteristics of the present invention, it is possible to provide an adhesive ejecting apparatus capable of applying adhesive in a small weight uniformly onto a to-be-joined member.

DETAILED DESCRIPTION

Hereinafter, a method of and an apparatus for manufacturing an absorbent article, according to one or more embodiments of the present invention, will be described with reference to the drawings.

Note that, in the following description of the drawings, same or similar reference signs denote same or similar elements and portions. In addition, it should be noted that the drawings are schematic are not to scale unless otherwise specified. Therefore, specific dimensions and the like should be determined in consideration of the following description. Moreover, the drawings do not necessarily reflect the real-life dimensional relationships and ratios of components.

First, a structure of an absorbent article 1 according to one or more embodiments will be described with reference to FIG. 1 which is a partially cutaway perspective view showing the absorbent article 1. In the particularly illustrated embodiment, the absorbent article 1 is a pants-type disposal diaper for adults.

Figure 1:
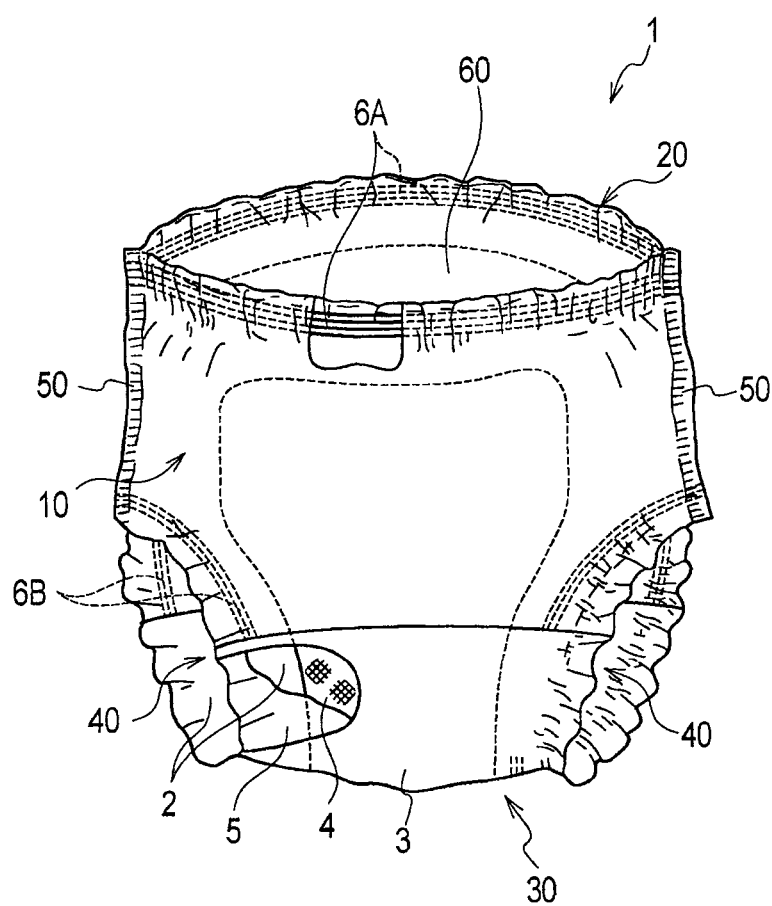
FIG. 1 is a partially cutaway, perspective view of an absorbent article according to one or more embodiments.

As shown in FIG. 1, the absorbent article 1 is formed mainly of a top sheet 2, a back sheet 3, an absorber 4, and a waterproof sheet 5.

The top sheet 2 is configured to come into contact with a skin of a person wearing the absorbent article 1 (hereinafter, referred to as "wearer"). As the top sheet 2, a liquid-permeable sheet, such as a non-woven fabric or a perforated plastic film, is used.

The back sheet 3 is provided outside of the top sheet 2, in other words, the back sheet is provided at the side farther from the wearer than top sheet 2. As the back sheet 3, a non-woven fabric or the like is used.

The absorber 4 is provided between the top sheet 2 and the back sheet 3, and is configured to absorb excretion of the wearer. As the absorber 4, a mixture of comminuted wood pulp and superabsorbent polymer particles, or the like, is used.

The waterproof sheet 5 is provided between the back sheet 3 and the absorber 4, and does not allow excretion of the wearer to permeate therethrough. The waterproof sheet 5 is a liquid-impermeable and moisture-permeable sheet that is impermeable to liquid but permeable to moisture.

The absorbent article 1 is provided with the top sheet 2, the absorber 4, the waterproof sheet 5 and the back sheet 3 in order, from the skin side of the wearer.

The absorbent article 1 as described above is formed by combining: a front waistline portion 10 to be fitted to the front waist of the wearer; a back waistline portion 20 to be fitted to the back waist of the wearer; and the crotch portion 30 to be fitted to the crotch of the wearer.

Note that, leg-surrounding openings 40 are formed respectively at sides of the crotch portion 30, and the legs of the wearer are to be inserted through the leg-surrounding openings 40.

The front waistline portion 10 and the back waistline portion 20 are united by joint portions 50, and thus form a waistline opening 60 to be fit around the body of the wearer.

A waist gather 6A made of rubber strands or the like having stretchability is provided in the peripheral edges of the front waistline portion 10 and the back waistline portion 20.

For example, the front waistline portion 10 and the back waistline portion 20 may be provided with the waist gather 6A to be thus stretchable in a cross direction crossing a front-to-back direction extending from the front waistline portion 10 to the back waistline portion 20, or may themselves be formed of sheets having stretchability to be thus stretchable in the cross direction.

The crotch portion 30 is provided between the front waistline portion 10 and the back waistline portion 20.

Leg gathers 6B each made of rubber strands or the like having stretchability are provided respectively at the sides of the crotch portion 30.

For example, the crotch portion 30 may be provided with the leg gathers 6B to be thus stretchable in the front-to-back direction of the absorbent article 1, or may itself be formed of a sheet having stretchability to be thus stretchable in the front-to-back direction of the absorbent article 1.

Next, a method of manufacturing an absorbent article 1 according to one or more embodiments will be described with reference to FIG. 2 which is an explanatory view for explaining a relevant part of the absorbent article manufacturing method.

Figure 2:
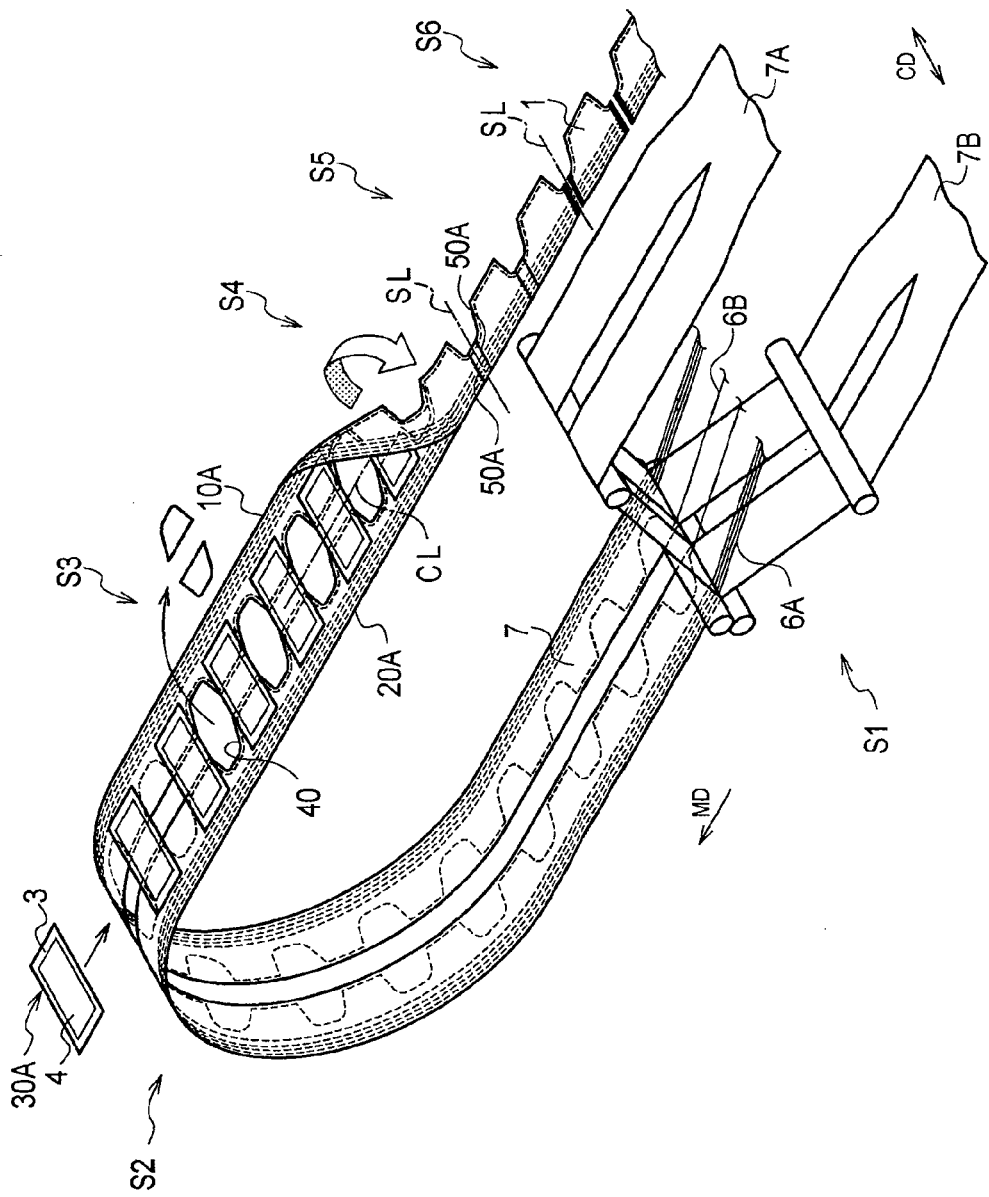
FIG. 2 is a diagram for explaining a method of manufacturing an absorbent article according to one or more embodiments.

As shown in FIG. 2, the method of manufacturing the absorbent article 1 includes at least a waistline forming step S1, an absorber transferring step S2, a leg-surrounding forming step S3, a folding step S4, a joining step S5, and a cutting step S6.

In the waistline forming step S1 a web 7 is formed by disposing gathers (the waist gather 6A and/or the leg gathers 6B) between a web 7A and a web 7B. The web 7 is to be processed into the front waistline portion 10 and the back waistline portion 20.

Note that, the web 7 (the webs 7A and 7B) being conveyed is stretchable in a cross direction CD (a width direction) orthogonal to a conveyance direction MD (Machine Direction) of the web 7.

In addition, the web 7 is asymmetrical with respect to a center line CL that bisects a width in the cross direction CD of the web 7 and extends in the conveyance direction MD of the web 7.

In the absorber transferring step S2, a crotch portion member 30A to be processed into the crotch portion 30 is transferred onto the web 7, specifically, between the front waistline portion 10 and the back waistline portion 20, after the waistline forming step S1. Note that, the crotch portion member 30A is formed of the back sheet 3 and the absorber 4.

In the leg-surrounding forming step S3, the leg-surrounding openings 40 (so-called leg holes) are formed by cutting the web 7 (the webs 7A and 7B) after the absorber transferring step S2.

Note that, the leg-surrounding openings 40 are not necessarily formed by cutting only the web 7 (the webs 7A and 7B), but may alternatively be formed by cutting the back sheet 3 forming the crotch portion member 30A together with the web 7A and the web 7B.

Here, the absorber transferring step S2 and the leg-surrounding forming step S3 may be performed in the reverse order.

In the folding step S4, the web 7 is folded in half along a folding line extending in the conveyance direction MD of the web 7, by bringing a side edge 10A of the front waistline portion 10 in the web 7 toward a side edge 20A of the back waistline portion 20 in the web 7, after the leg-surrounding forming step S3.

Note that, in the particularly illustrated embodiment, the folding line is the same as the center line CL. Moreover, the folding line does not necessarily coincide with the center line CL, and may be offset from the center line CL toward the side edge 10A or toward the side edge 20A.

In the joining step S5, the folded parts of the web 7 are joined at joint regions 50A to be processed into the joint portions 50 of the absorbent article 1 by an ultrasonic treatment or a heat treatment, after the folding step S4.

Note that the joint regions 50A respectively indicate regions at both sides of an imaginary line SL in the conveyance direction MD. The imaginary line SL indicates a cutting line extending in the width direction CD.

In the cutting step S6, the web 7 in which the joint regions 50A have been joined is cut along the imaginary line SL after the joining step S5. As a result, the absorbent article 1 is manufactured.

In the waistline forming step S1, the web 7A and the web 7B are overlaid one upon another, sandwiching the waist gathers 6A and/or the leg gathers 6B therebetween. Then, the web 7A and the web 7B are joined to each other with adhesive or the like.

In addition, in the absorber transferring step S2, the crotch portion member 30A transferred onto the web 7 (the web formed of the overlaid webs 7B and 7A) having the leg-surrounding openings 40 formed therein is joined to the web 7 with adhesive or the like.

Herein below, a description will be given of an apparatus for use in any step in which webs are joined to each other or a web and a member (a sheet or a gather) are joined to each other, such as the waistline forming step S1 and the absorber transferring step S2.

Figure 3:
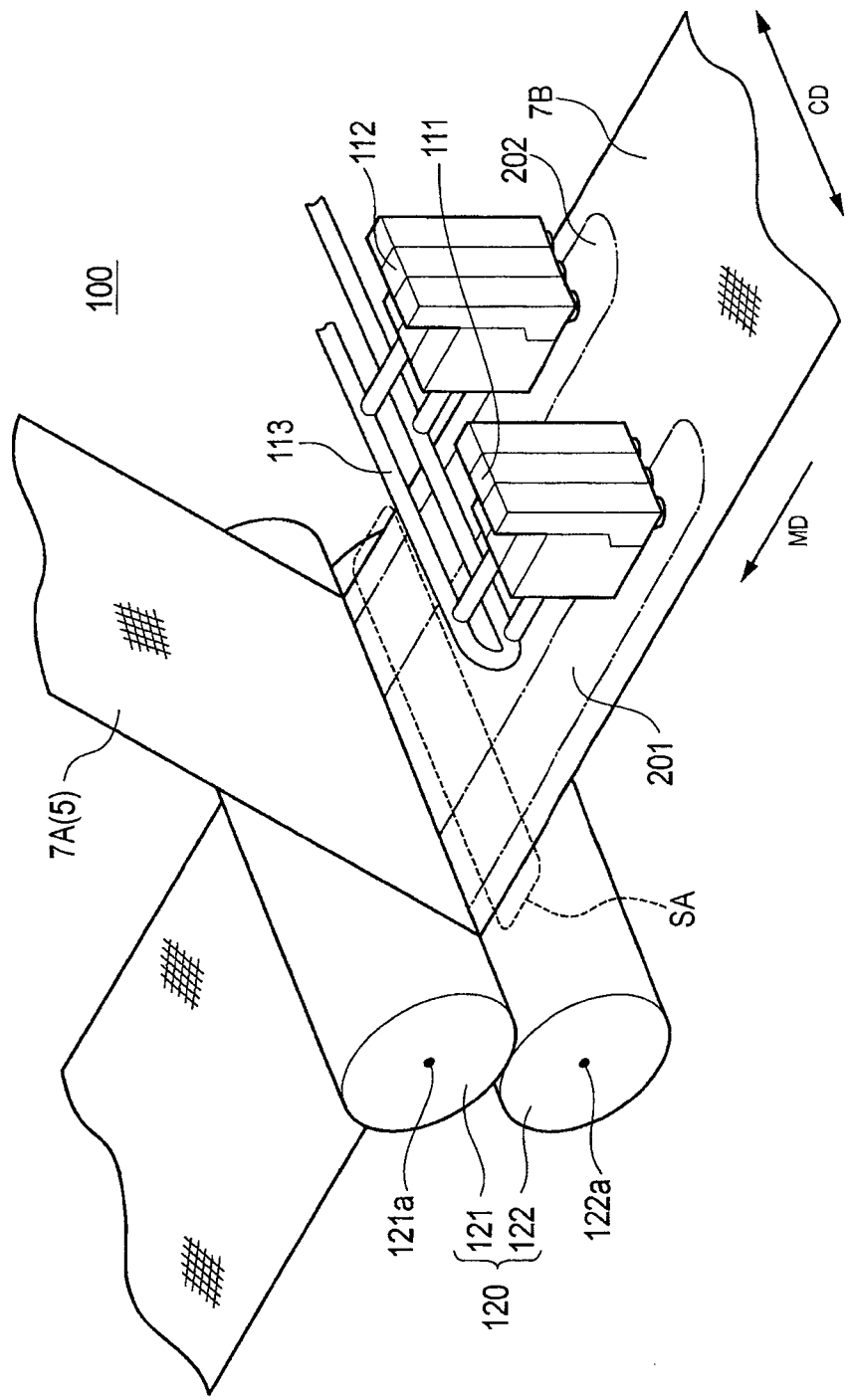
FIG. 3 is a perspective view of a relevant part of an apparatus for manufacturing an absorbent article according to one or more embodiments.

FIG. 3 is a perspective view of a relevant part of an adhesive ejecting apparatus 10 for manufacturing the absorbent article 1 according to one or more embodiments.

Figure 4:
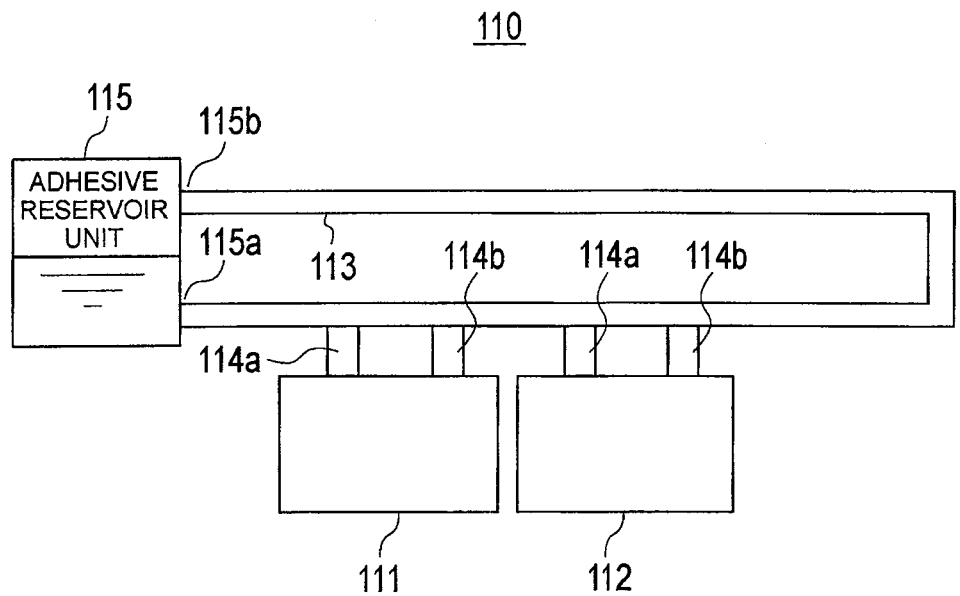
FIG. 4 is a schematic view of an adhesive ejecting apparatus according to one or more embodiments.

The adhesive ejecting apparatus 100 includes ejecting mechanisms 111 and 112 each configured to eject a flowable adhesive onto the web 7B, thereby applying the adhesive to the web 7B. A pipe 113 is connected to each of the ejecting mechanisms 111 and 112. The adhesive is supplied to the pipe 113 from an adhesive reservoir unit 115, which is shown in FIG. 4.

In the some embodiments, the adhesive ejecting apparatus 100 includes a plurality of ejecting mechanisms. The ejecting mechanism 111 and the ejecting mechanism 112 are arranged in parallel in the cross direction CD (the width direction of the web 7B) orthogonal to the conveyance direction MD of the web 7B.

In the adhesive ejecting apparatus 100, each of the ejecting mechanism 111 and the ejecting mechanism 112 is configured to eject a flowable adhesive onto the web 7B. In other words, each of the ejecting mechanism 111 and the ejecting mechanism 112 is capable of placing the adhesive on the web 7B without coming into contact with the web 7B.

The adhesive ejected from the ejecting mechanism 111 forms an adhesion region 201 on the web 7B. The adhesive ejected from the ejecting mechanism 112 forms an adhesion region 202 on the web 7B.

In other words, the ejecting mechanism 111 and the ejecting mechanism 112 are configured to perform an application step in the conveyance direction MD of the web 7B, in which the adhesive is applied onto the web 7B continuously in the conveyance direction MD.

Figure 5:
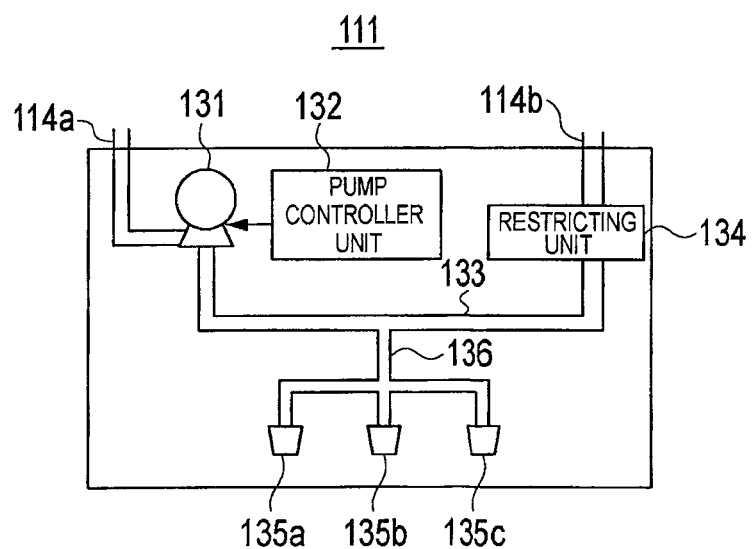
FIG. 5 is a schematic view for explaining a configuration of an application mechanism in accordance with one or more embodiments.

Each of the ejecting mechanism 111 and the ejecting mechanism 112 includes adhesive nozzles 135a to 135c (shown in FIG. 5).

In addition, each of the ejecting mechanism 111 and the ejecting mechanism 112 includes air nozzles (not shown) configured to blow air in a plurality of directions to the adhesive ejected from the adhesive nozzles.

Each of the ejecting mechanism 111 and the ejecting mechanism 112 is configured to change the trajectory of the adhesive in the air, by blowing air as appropriate in a plurality of directions to the adhesive ejected from the adhesive nozzles.

This configuration enables each of the ejecting mechanism 111 and the ejecting mechanism 112 to change the shape of the adhesive placed on the web 7B.

In the particularly illustrated embodiment shown in FIG. 3, a press mechanism 120 is disposed adjacent to the adhesive ejecting apparatus 100. The press mechanism 120 is configured to place the web 7A or an absorber onto the web 7B having the adhesive applied thereonto, and then to press the webs 7A and 7B against each other.

The press mechanism 120 includes an upper roller 121 and a lower roller 122.

The upper roller 121 and the lower roller 122 are configured to hold the web 7B and the web 7A which is overlaid with the web 7B from above and/or below.

The upper roller 121 and the lower roller 122 are configured to press the web 7A and the web 7B against each other, by holding the web 7A and the web 7B in a direction crossing the plane of the webs 7A and 7B.

The upper roller 121 and the lower roller 122 form a pressing region extending in a direction crossing the conveyance direction MD on the webs 7A and 7B.

In the embodiment, a rotational axis 121a of the upper roller 121 and a rotational axis 122a of the lower roller 122 are parallel to the cross direction CD orthogonal to the conveyance direction MD.

The press mechanism 120 is configured to perform a pressing step in which the overlaid webs 7A and 7B are pressed against each other in the pressing region extending in the cross direction CD.

In FIG. 3, an example of the web 7B is the back sheet 3, and an example of the web 7A is the waterproof sheet 5. A step of placing one or more elastic members (e.g., a gather 6) on the adhesion region 201 and/or the adhesion region 202 formed on the back sheet 3 may be subsequently executed.

Next, the configuration of the adhesive ejecting apparatus 100 will be described in detail with reference to FIG. 4 which is a schematic view of the adhesive ejecting apparatus 100.

The adhesive ejecting apparatus 100 includes the adhesive reservoir unit 115, the pipe 113, the ejecting mechanism 111, and the ejecting mechanism 112.

Adhesive is stored in the adhesive reservoir unit 115. The pipe 113 is connected to the adhesive reservoir unit 115, and the adhesive stored in the adhesive reservoir unit 115 is caused to flow through the pipe 113.

In addition, the pipe 113 is provided with a heating portion (not shown) configured to heat the adhesive flowing through the pipe 113. Each of the ejecting mechanism 111 and the ejecting mechanism 112 is connected to the pipe 113, and is configured to eject the adhesive toward the web 7A. Here, the pipe 113 constitutes a flow pipe.

Thermoplastic polymer materials of a rubber group or an olefin group can be used as the adhesive, and mainly the rubber group can be used. Although the melting temperature varies depends on the material, normally an adhesive which is solid at 40° C. or less, and which melts in a range from 65° C. to 150° C., can be used. Viscosity of the adhesive can be 10,000 cps or less and normally it is between 2,000 cps to 5,000 cps.

The adhesive reservoir unit 115 has an outlet 115a and an inlet 115b formed therein.

The outlet 115a is connected to one end of the pipe 113, and the adhesive stored in the adhesive reservoir unit 115 is sent out to the ejecting mechanism 111 and the ejecting mechanism 112 through the outlet 115a.

The inlet 115b is connected to the other end of the pipe 113, and the adhesive flowing through the pipe 113 is returned to the adhesive reservoir unit 115 through the inlet 115b.

Each of the ejecting mechanism 111 and the ejecting mechanism 112 includes: an intake pipe 114a through which the adhesive is taken from the pipe 113; and a discharge pipe 114b through which excess adhesive is sent out to the pipe 113.

Note that, the adhesive reservoir unit 115 in the embodiment constitutes a reservoir unit; the pipe 113 in the embodiment constitutes a flow pipe; and the web 7B in the embodiment constitutes a to-be-joined member.

Next, the configuration of each of the ejecting mechanism 111 and the ejecting mechanism 112 will be described in detail with reference to FIG. 5.

FIG. 5 is a schematic view of each of the ejecting mechanism 111 and the ejecting mechanism 112. In some embodiments, the ejecting mechanism 111 and the ejecting mechanism 112 may be used interchangeably without being distinguished from each other. Accordingly, the configuration of the ejecting mechanism 111 will be described below.

The ejecting mechanism 111 includes a pump 131, a pump controller unit 132, a distribution pipe 133, a restricting unit 134, and adhesive nozzles 135a to 135c. In the particularly illustrated embodiment, the ejecting mechanism 111 includes three nozzles.

The pump 131 is configured to take the adhesive flowing through the pipe 113 into the ejecting mechanism 111 through the intake pipe 114a. The pump controller unit 132 is configured to control an increase or decrease in the amount of adhesive to be taken in by the pump 131. In other words, the pump 131 and the pump controller unit 132 constitute a supply unit.

The distribution pipe 133 is configured to send a predetermined amount of adhesive to the adhesive nozzles 135a to 135c from the supply unit. The distribution pipe 133 is also configured to send any unused amount of the supplied adhesive to the discharge pipe 114b. The distribution pipe 133 constitutes a distribution unit.

The restricting unit 134 is disposed between the distribution pipe 133 and the discharge pipe 114b, and is configured to restrict the amount of adhesive to return to the pipe 113. In one or more embodiments, restricting unit 134 is a controllable valve.

In one or more embodiments, the restricting unit 134 has such a structure that the amount of adhesive returned to the pipe 113 is adjustable. The opening and closing of the restricting unit 134 is controlled by an unillustrated controller unit. In some embodiments, the pump controller 132 is also configured to control the restricting unit 134.

Each of the adhesive nozzles 135a to 135c applies the adhesive onto the web 7B in a predetermined pattern while not coming into contact with the web 7B. The adhesive nozzles 135a to 135c constitute an ejector unit.

In the above-described configuration, the pump 131 and the pump controller unit 132 are configured to take in, from the pipe 113, the adhesive in an amount larger than a specified ejection amount of adhesive to be ejected from each of the adhesive nozzles 135a to 135c, and to supply the adhesive thus taken in to each of the adhesive nozzles 135a to 135c.

In some embodiments, when the specified ejection amount for one adhesive nozzle is 100%, the pump 131 and the pump controller unit 132 are configured to take in the adhesive in an amount of 120% of the specified ejection amount for each adhesive nozzle. In one or more embodiments, restricting unit 134 may be measured by a mass-flow sensor which is not shown in the figure.

In the particularly illustrated embodiment, the ejecting mechanism 111 includes three adhesive nozzles 135a to 135c, each of which ejects the same amount of adhesive. Accordingly, the adhesive in an amount of 360% of the specified ejection amount is taken in from the pipe 113.

The distribution pipe 133 is configured to send the specified ejection amount of adhesive to each of the adhesive nozzles 135a to 135c from the adhesive supplied by the pump 131, and to also supply the rest, that is, 20% of the adhesive back to the pipe 113 all the time during operation.

In the embodiment, a distribution pipe 136 is further connected between the distribution pipe 133 and the adhesive nozzles 135a to 135c.

The distribution pipe 136 may be formed to have an inner diameter smaller than that of the distribution pipe 133. With the distribution pipe 133, the distribution pipe 136, and the controllable opening of the restricting unit 134, it is possible to adjust the amount of adhesive to be returned to the pipe 113 and the amount of adhesive to be ejected from each of the adhesive nozzles 135a to 135c.

In one or more embodiments, the specified ejection amount is in a coating weight of 1 $g/m^2$ to 20 $g/m^2$. For example, a spray coating nozzle for coating an adhesive without contact with a coating object can be used as the adhesive nozzles 135a to 135c. Specifically, a spiral coating nozzle that enables a continuous spiral coating can be used. An ejecting amount of the adhesive can be adjusted by these nozzles.

If the weight falls below 1 $g/m^2$, a secure bonding becomes difficult. On the other hand, if the weight exceeds 20 $g/m^2$, the wear comfort of the product is deteriorated. Moreover, if the weight exceeds 20 $g/m^2$, the air permeability of the product is reduced. In further embodiments, the specified $g/m^2$ to 10 $g/m^2$ in terms of coating weight. Further, the ejection amount can be set from 2 $g/m^2$ to 8 $g/m^2$ in terms of coating weight.

As described above, in each of the ejecting mechanism 111 and the ejecting mechanism 112 in the adhesive ejecting apparatus 100, part of the adhesive taken into the ejecting mechanism 111 and the ejecting mechanism 112 from the pipe 113 is always returned to the pipe 113. In other words, the adhesive always circulates between the inside of the pipe 113 and the adhesive reservoir unit 115.

Accordingly, when the adhesive nozzles 135a to 135c are intermittently used, it is possible to reduce the difference in internal pressure between the time at which the adhesive nozzles 135a to 135c are opened and the time at which the adhesive nozzles 135a to 135c are closed. As a result, the adhesive can be applied in a small weight uniformly onto the to-be-joined member.

In the application step where the adhesive nozzles 135a to 135c are individually and intermittently used, the internal pressure applied in each of the adhesive nozzles 135a to 135c varies depending on whether all or some of the adhesive nozzles 135a to 135c are used.

For this reason, it has been difficult to make constant the amount of adhesive ejected from each of the adhesive nozzles 135a to 135c, by changing the pressure to be applied to each of the adhesive nozzles 135a to 135c.

In this regard, the adhesive ejecting apparatus 100 according to the embodiment includes the supply unit to control an increase or decrease in the amount of adhesive to be taken in and the distribution unit to return an excess of the adhesive to the pipe 113 all the time.

Accordingly, the adhesive ejecting apparatus 100 is capable of reducing the difference among the internal pressures generated in the respective adhesive nozzles 135a to 135c even in the application step where the adhesive nozzles 135a to 135c are individually and intermittently used. As a result, the adhesive can be applied in a small weight uniformly onto the to-be-joined member.

Using the adhesive ejecting apparatus 100 enables the application of adhesive in a small coating amount on the to-be-joined member in manufacturing absorbent articles. Accordingly, it is possible to securely join sheets, or a sheet and another member, to each other without deteriorating the moisture-permeability of the article.

In addition, since the adhesive ejecting apparatus 100 is capable of the application with a small coating amount, the adhesive ejecting apparatus 100 can join materials, including a sheet and another member, to each other without deteriorating the flexibility of the materials even when the adhesive is applied to the materials.

As a result, the adhesive ejecting apparatus 100 is capable of manufacturing absorbent articles without deteriorating the wear comfort and texture of the product.

As described above, the details of several embodiments have been exemplarily disclosed. However, it should not be understood that the description and drawings which constitute part of this disclosure limit the present invention. From this disclosure, various alternative embodiments, examples, and operation techniques will be easily found by those skilled in the art.

Although the case where the adhesive ejecting apparatus 100 includes two ejecting mechanisms 111 and 112 has been described in the foregoing description, the adhesive ejecting apparatus 100 may include only one ejecting mechanism, or may include more than two ejecting mechanisms.

Although the case where the ejecting mechanism 111 includes three adhesive nozzles 135a to 135c has been described, the ejecting mechanism 111 may include only one or two adhesive nozzles, or may include more than three adhesive nozzles.

Further, the absorbent article manufactured in accordance with the present invention is not limited to a disposable diaper, but may be an absorbent article such as a sanitary napkin or a panty liner, for example, and also may be any product other than absorbent articles.

As described above, the present invention naturally includes various embodiments which are not described herein. Accordingly, the technical scope of the present invention should be determined only by the matters to define the invention in the scope of claims regarded as appropriate based on the description.

The entire content of Japanese Patent Applications 2009-048653 (filed on Mar. 2, 2009) and 2010-041933 (filed on Feb. 26, 2010) are incorporated herein by reference.

INDUSTRIAL APPLICABILITY

Therefore, since the adhesive ejecting apparatus of the present invention provides an adhesive ejecting apparatus capable of applying adhesive in a small weight uniformly onto a to-be-joined member, it is useful in manufacturing technology for absorbent articles.

REFERENCE SIGNS LIST 1 absorbent article
2 top surface sheet
3 bottom surface sheet
4 absorber
5 waterproof sheet
6 gather
6A waist gather
6B leg gather
7A, 7B web
10 front waistline portion
20 back waistline portion
30 crotch portion
40 leg-surrounding openings
50 joint portion
50A joint region
60 waistline openings
100 adhesive ejecting apparatus
111, 112 ejecting mechanism
113 pipe
114a intake pipe
114b discharge pipe
115 adhesive reservoir
115a outlet
115b inlet
120 press mechanism
121 upper roller
121a rotational axis
122 lower roller
122a rotational axis
131 pump
132 pump controller
133 distribution pipe
134 restricting unit
135a to 135c adhesive nozzle
136 distribution pipe
201 adhesion region
202 adhesion region

The invention claimed is:

1. An adhesive ejecting apparatus, comprising:
a reservoir unit configured to store adhesive to be applied onto a to-be-joined member;
a flow pipe connected to the reservoir unit and through which the adhesive stored in the reservoir unit flows; and
at least an ejecting mechanism connected to the flow pipe and configured to eject the adhesive toward the to-be-joined member,
wherein
the reservoir unit comprises:
an outlet through which the adhesive stored in the reservoir unit is sent out to the ejecting mechanism; and
an inlet through which the adhesive flowing through the flow pipe is returned to the reservoir unit,
one end of the flow pipe is connected to the outlet,
another end of the flow pipe is connected to the inlet,
the ejecting mechanism comprises:
at least an ejector unit configured to eject the adhesive toward the to-be-joined member;
a supply unit configured to supply the ejector unit with the adhesive flowing from the flow pipe;
a distribution unit configured to send a predetermined amount of adhesive supplied by the supply unit to the ejector unit, and to return the rest of the supplied adhesive to the flow pipe; and
a restricting unit disposed between the distribution unit and the flow pipe and configured to restrict an amount of adhesive to be returned to the flow pipe,
the supply unit is configured to supply adhesive from the flow pipe to the ejector unit in an amount larger than a specified ejection amount of adhesive to be ejected by the ejector unit,
the flow pipe and the adhesive reservoir unit define a first flow path for circulating the adhesive therethrough,
the flow pipe, the adhesive reservoir unit, and the ejecting mechanism define a second flow path for circulating the adhesive therethrough,
the restricting unit of the ejecting mechanism is within the second flow path but outside the first flow path,
in the second flow path, the supply unit is upstream of the distribution unit, the ejector unit is coupled to the distribution unit, and the restricting unit is downstream of the distribution unit,
the supply unit includes a pump and a pump controller,
the distribution unit includes
a first pipe connecting the pump and the restricting unit, and
a second pipe connecting the ejector unit to the first pipe at a location upstream of the restriction unit and downstream of the pump.

2. The adhesive ejecting apparatus according to claim 1, wherein
the ejecting mechanism includes a plurality of the ejector units; and
the distribution unit is configured to distribute the adhesive supplied from the supply unit to the plurality of ejector units.

3. The adhesive ejecting apparatus according to claim 1, further comprising a plurality of the ejecting mechanisms having a plurality of corresponding restricting units,
wherein the ejecting mechanisms are arranged in parallel to each other in a direction orthogonal to a conveyance direction of the to-be-joined member, wherein the ejecting mechanisms define, together with the flow pipe and the adhesive reservoir unit, a plurality of corresponding second flow paths, and wherein each of the plurality of restricting units is within the corresponding second flow path, but outside the first flow path and the other second flow paths.

4. The adhesive ejecting apparatus according to claim 1, wherein
the restricting unit is configured to adjust the amount of adhesive to be returned to the flow pipe.

5. The adhesive ejecting apparatus according to claim 1, wherein
the ejecting mechanism is configured to apply adhesive onto the to-be-joined member in a weight of 1 g/m$^2$ to 10 g/m$^2$.

6. The adhesive ejecting apparatus according to claim 1, wherein
the to-be-joined member is a web formed of a continuous material for forming part of an absorbent article; and
the ejecting mechanism is configured to eject the adhesive toward the web continuously moved in a longitudinal direction thereof as the conveyance direction.

7. The adhesive ejecting apparatus according to claim 6, wherein
the absorbent article includes at least a moisture-permeable sheet that is permeable to moisture; and
the to-be-joined member is the moisture-permeable sheet.

8. The adhesive ejecting apparatus according to claim 6, wherein
the absorbent article is a pants-type diaper; and
the ejecting mechanism is configured to eject the adhesive toward the web in a region to be processed into at least a front waistline portion and a rear waistline portion of the pants-type diaper.

9. An adhesive ejecting apparatus, comprising:
a reservoir unit configured to store adhesive to be applied onto a to-be-joined member;
a flow pipe connected to the reservoir unit and through which the adhesive stored in the reservoir unit flows; and
at least an ejecting mechanism connected to the flow pipe and configured to eject the adhesive toward the to-be-joined member,
wherein
the reservoir unit comprises:
an outlet through which the adhesive stored in the reservoir unit is sent out to the ejecting mechanism; and
an inlet through which the adhesive flowing through the flow pipe is returned to the reservoir unit,
one end of the flow pipe is connected to the outlet,
another end of the flow pipe is connected to the inlet,
the ejecting mechanism comprises:
at least an ejector unit configured to eject the adhesive toward the to-be-joined member;
a supply unit configured to supply the ejector unit with the adhesive flowing from the flow pipe;
a distribution unit configured to send a predetermined amount of adhesive supplied by the supply unit to the ejector unit, and to return the rest of the supplied adhesive to the flow pipe; and
a restricting unit disposed between the distribution unit and the flow pipe and configured to restrict an amount of adhesive to be returned to the flow pipe,
the supply unit is configured to supply adhesive from the flow pipe to the ejector unit in an amount larger than a specified ejection amount of adhesive to be ejected by the ejector unit,
the flow pipe and the adhesive reservoir unit define a first flow path for constantly circulating the adhesive therethrough when the adhesive ejecting apparatus is on,
the flow pipe, the adhesive reservoir unit, and the ejecting mechanism define a second flow path for circulating the adhesive therethrough,
the restricting unit of the ejecting mechanism is within the second flow path but outside the first flow path,
in the second flow path, the supply unit is upstream of the distribution unit, the ejector unit is coupled to the distribution unit, and the restricting unit is downstream of the distribution unit,
the supply unit includes a pump and a pump controller,
the distribution unit includes
a first pipe connecting the pump and the restricting unit, and
a second pipe connecting the ejector unit to the first pipe at a location upstream of the restriction unit and downstream of the pump.

10. The adhesive ejecting apparatus according to claim 1, wherein
the flow pipe and the adhesive reservoir unit are configured to constantly circulate the adhesive in the first flow path when the adhesive ejecting apparatus is on.

11. The adhesive ejecting apparatus according to claim 1, wherein the restricting unit of the ejecting mechanism is configured to adjust pressure at the ejector unit and to adjust the amount of adhesive to be ejected.

12. The adhesive ejecting apparatus according to claim 9, wherein the restricting unit of the ejecting mechanism is configured to adjust pressure at the ejector unit and to adjust the amount of adhesive to be ejected.

* * * * *